United States Patent [19]

Quallich et al.

[11] Patent Number: 4,839,104
[45] Date of Patent: Jun. 13, 1989

[54] PROCESS FOR PREPARING SERTRALINE INTERMEDIATES

[75] Inventors: George J. Quallich, North Stonington, Conn.; Michael T. Williams, Deal, England

[73] Assignee: Pfizer, Inc., New York, N.Y.

[21] Appl. No.: 207,579

[22] Filed: Jun. 16, 1988

Related U.S. Application Data

[63] Continuation-in-part of Ser. No. 60,577, Jun. 11, 1987, Pat. No. 4,777,288.

[51] Int. Cl.$^4$ ............................................. C07C 97/18
[52] U.S. Cl. ............................................... 260/396 R
[58] Field of Search ..................... 260/396 K, 396 N

[56] References Cited

U.S. PATENT DOCUMENTS 4,536,518  8/1985  Welch, Jr. et al. ................. 514/647
4,556,676 12/1985  Welch et al. ....................... 514/554

FOREIGN PATENT DOCUMENTS 28901  5/1981  European Pat. Off. .
30081  6/1981  European Pat. Off. .
2632862  2/1977  Fed. Rep. of Germany .

OTHER PUBLICATIONS

Heaney, H. et al., J. Chem. Soc., Parkin Trans. 1(23) 2698–701, 1974.
W. M. Welch, Jr. et al., *Journal of Medicinal Chemistry*, vol. 27, No. 11, p. 1508 (1984).
E. A. Stech et al., *Journal of the American Chemical Society*, vol. 75, p. 1117 (1953).
D. L. Boger et al., *Tetrahedron Letters*, vol. 25, No. 49, p. 1516 (1984).
C. S. Rao et al., in the *Indian Journal of Chemistry*, Sec. B 25B(b), p. 626 (1986).

*Primary Examiner*—Paul J. Killos
*Attorney, Agent, or Firm*—Peter C. Richardson; Lawrence C. Akers; Paul H. Ginsburg

[57] ABSTRACT

A novel three-step process for preparing 4-(3,4-dichlorophenyl)-4-phenylbutanoic acid is disclosed, which involves (1) reducing 4-(3,4-dichlorophenyl)-4-ketobutanoic acid to 4-(3,4-dichlorophenyl)-4-hydroxybutanoic acid; (2) then converting the intermediate hydroxy acid formed in the first step to 5-(3,4-dichlorophenyl)-dihydro-2(3H)-furanone, and (3) thereafter reacting the resulting gamma-butyrolactone compound with benzene in a Friedel-Crafts type reaction to form the desired final product. The latter compound is known to be useful as an intermediate leading to 4-(3,4-dichlorophenyl)-3,4-dihydro-1(2H)-naphthalenone and ultimately, to cis-(1S)(4S)-N-methyl-4-(3,4-dichlorophenyl)-1,2,3,4-tetrahydro-1-naphthalene amine (sertraline), which is known to be a preferred anti-depressant agent in the field of medicinal chemistry. The aforementioned 5-(3,4-dichlorophenyl)-dihydro-2(3H)-furanone and 4-(3,4-dichlorophenyl)-4-hydroxybutanoic acid are both novel compounds. There is also disclosed a novel process for converting 5-(3,4-dichlorophenyl)-dihydro-2(3H)-furanone directly to 4-(3,4-dichlorophenyl)-3,4-dihydro-1(2H)-naphthalenone, as well as an alternate novel process for converting 4-(3,4-dichlorophenyl)-4-hydroxybutanoic acid directly to this same key intermediate.

19 Claims, No Drawings

PROCESS FOR PREPARING SERTRALINE INTERMEDIATES

CROSS REFERENCE TO RELATED APPLICATION

This application is a continuation-in-part of co-pending application Ser. No. 07/60,577, filed June 11, 1987 now U.S. Pat. No. 4,777,288.

BACKGROUND OF THE INVENTION

This invention relates to a new and useful process for preparing a known 4,4-diphenylbutanoic acid derivative. More particularly, it is concerned with a novel three-step process for preparing 4-(3,4-dichlorophenyl)-4-phenylbutanoic acid, which serves as a key intermediate in the production of the antidepressant agent known as cis-(1S)(4S)-N-methyl-4-(3,4-dichlorophenyl)1,2,3,4-tetrahydro-1-naphthaleneamine (sertraline) via 4-(3,4-dichlorophenyl)-3,4-dihydro-1(2H)-naphthalenone. The invention also includes within its scope such novel compounds as 4-(3,4-dichlorophenyl)-4-hydroxybutanoic acid and 5-(3,4-dichlorophenyl)-dihydro-2(3H)-furanone, which are used as intermediates in the aforesaid three-step novel process. The invention additionally includes a novel process for converting both 4-(3,4-dichlorophenyl)-4-hydroxybutanoic acid and 5-(3,4-dichlorophenyl)-dihydro-2(3H)-furanone directly to the aforesaid 4-(3,4-dichlorophenyl)-3,4-dihydro-1(2H)naphthalenone.

In accordance with the prior art, there is described in U.S. Pat. No. 4,536,518 to W. M. Welch, Jr. et al., as well as in the paper of W. M. Welch, Jr. et al. appearing in the *Journal of Medicinal Chemistry*, Vol. 27, No. 11, p. 1508 (1984), a method for preparing certain 4-(substituted phenyl)-4-(optionally-substituted phenyl)-butanoic acids wherein the optional substituent is always other than alkoxy. These particular 4,4-diphenylbutanoic acid derivatives are shown to be useful as intermediates that lead to various antidepressant derivatives of cis-4-phenyl-1,2,3,4-tetrahydro-1-naphthaleneamine, including cis-(1S)(4S)-N-methyl-4-(3,4-dichlorophenyl)-1,2,3,4-tetrahydronaphthaleneamine (sertraline) which is an especially preferred embodiment in this series. The prior art method disclosed in the aforesaid publications of W. M. Welch, Jr. et. al. involves synthesizing the desired 4,4-diphenylbutanoic acid intermediates in a plurality of steps starting from the corresponding benzophenone compound. For instance, the appropriately substituted benzophenone starting material is first subjected to a base-catalyzed Stobbe condensation with diethyl succinate, followed by hydrolysis and decarboxylation with 48% aqueous hydrobromic acid to yield the corresponding 4,4-diphenylbut-3-enoic acid, which is thereafter reduced by catalytic hydrogenation or by the use of hydriodic acid and red phosphorus to finally yield the desired 4,4-diphenylbutanoic acid intermediate.

SUMMARY OF THE INVENTION

In accordance with the present invention, there is now provided a new and improved process for preparing 4-(3,4-dichlorophenyl)-4-phenylbutanoic acid, known to be useful as an intermediate as hereinbefore discussed, by a novel three-step method starting from 4-(3,4-dichlorophenyl)-4-ketobutanoic acid whereby the desired final product is readily obtained in pure form and in high yield. More particularly, the novel three-step method of the invention is directed to a process for preparing a compound of the formula:

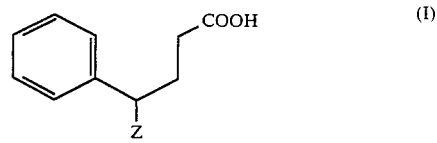

wherein Z is 3,4-dichlorophenyl, i.e., the compound known as 4-(3,4-dichlorophenyl)-4-phenylbutanoic acid, which comprises the steps of:

(a) subjecting 4-(3,4-dichlorophenyl)-4-ketobutanoic acid of the formula:

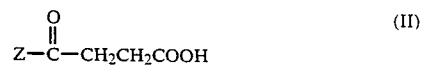

wherein Z is as previously defined, to the selective action of a carbonyl reducing agent in a polar protic solvent or an aprotic solvent at a temperature of from about 0° C. to about 100° C. until the reduction reaction to form the desired 4-(3,4-dichlorophenyl)-4-hydroxybutanoic acid intermediate is substantially complete;

(b) converting the intermediate hydroxy acid formed in step (a) to the corresponding dihydro-2(3H)furanone compound of the formula

wherein Z is as previously defined; and (c) thereafter reacting the resulting gammabutyrolactone compound formed in step (b) with benzene in an excess of said reagent as solvent or in a reaction-inert organic solvent in the presence of a Friedel-Crafts type catalyst at a temperature of from about 0° C. to 100° C. until the alkylation of benzene by the aforesaid gamma-lactone compound of formula (III) to form the desired final product of formula (I) is substantially complete.

In this way, compound such as 4-(3,4-dichlorophenyl)-4-ketobutanoic acid is readily converted, via the novel intermediates 4-(3,4-dichlorophenyl)-4-hydroxybutanoic acid and 5-(3,4-dichlorophenyl)dihydro-2(3H)-furanone, respectively, to 4-(3,4-dichlorophenyl)-4-phenylbutanoic acid in a most facile manner. As previously indicated, the latter-named final product is known to be useful as a valuable intermediate in the production of the antidepressant agent sertraline, which is cis-(1S)(4S)-N-methyl-4-(3,4-dichlorophenyl)-1,2,3,4-tetrahydro-1-naphthaleneamine [see U.S. Pat. No. 4,536,518 as well as *Journal of Medicinal Chemistry*, Vol. 27, No. 11, p. 1508 (1984)].

Accordingly, there is also included within the purview of this invention the novel gamma-butyrolactone compound produced in step (b), which is useful as an intermediate for the production of the final product hereinbefore described. The present invention therefore includes the novel 5-(substituted phenyl)dihydro-2(3H)-furanone compound of the formula:

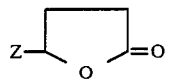 (III)

wherein Z is 3,4-dichlorophenyl, i.e., the compound designated as 5-(3,4-dichlorophenyl)-dihydro-2(3H)furanone. This particular 5-(substituted phenyl)-dihydro-2(3H)-furanone is the intermediate that specifically leads to 4-(3,4-dichlorophenyl)-4-phenylbutanoic acid and ultimately, to sertraline as previously discussed.

Additionally, the invention also includes within its purview the novel compound designated as b 4-(3,4-dichlorophenyl)-4-hydroxybutanoic acid, which is used as a starting material in step (b) to produce the aforesaid novel gamma-butyrolactone intermediate per se. Accordingly, the present invention also includes the novel hydroxy acid compound of the formula:

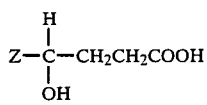 (IV)

and its alkali metal and amine addition salts, wherein Z is 3,4-dichlorophenyl. This particular acid is the key starting material in step (b) that serves as a useful intermediate in the synthesis which ultimately leads to sertraline.

Also disclosed within the purview of this invention is a novel process for converting 5-(3,4-dichlorophenyl)-dihydro-2(3H)-furanone directly to 4-(3,4-dichlorophenyl)-3,4-dihydro-1(2H)-naphthalenone, as well as an alternate novel process for converting 4-(3,4-dichlorophenyl)-4-hydroxybutanoic acid directly to this same key intermediate. More particularly, the novel conversion process involves reacting a compound of the formula:

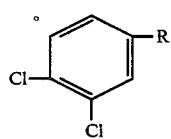 (V)

wherein R is

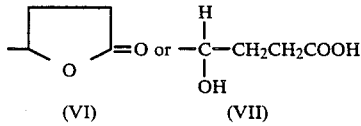

(VI)        (VII)

with benzene in an excess of said reagent as solvent or in a reaction-inert organic solvent in the presence of a protic or Lewis acid catalyst at a temperature of from about −20° C. to about 180° C. until the alkylation of benzene by either the aforesaid hydroxy acid or the corresponding gamma-butyrolactone compound, followed by ring closure to form the desired ring ketone final product is substantially complete.

In this way, a known compound such as the ultimate starting material which is 4-(3,4-dichlorophenyl)-4-keto-butanoic acid is readily converted, via the novel intermediates, viz., 4-(3,4-dichlorophenyl)-4-hydroxybutanoic acid or 5-(3,4-dichlorophenyl)-dihydro-2(3H)furanone, to 4-(3,4-dichlorophenyl)-3,4-dihydro-1(2H)naphthalenone in a most facile manner. As previously indicated, the latter-named final product is also known to be useful as a valuable intermediate in the production of the antidepressant agent sertraline.

DETAILED DESCRIPTION OF THE INVENTION

In accordance with the process of this invention, the reduction of 4-(3,4-dichlorophenyl)-4-ketobutanoic acid to 4-(3,4-dichlorophenyl)-4-hydroxybutanoic acid in step (a) is accomplished by using a carbonyl reducing agent that is capable of reducing a ketone in the presence of a carboxylic acid or a salt thereof. This category includes alkali metal borohydrides and related reagents, amineboranes and lithium aluminum hydride derived reagents and dialkylaluminum hydride reagents. In general, the reduction step is carried out in a polar protic or an aprotic solvent at a temperature of from about 0° C. to about 100° C. until the reduction reaction to form the desired 4-hydroxy compound is substantially complete. Preferred polar protic solvents for use in this connection include water and lower alkanols ($C_1$-$C_4$) such as methanol, ethanol and isopropanol, etc., while preferred aprotic solvents include acetonitrile, dimethylformamide, diethylformamide, dimethylacetamide, dioxane, tetrahydrofuran, benzene and the like. The latter type solvents are especially preferred when using reagents other than the alkali metal borohydrides. A preferred embodiment involves the use of an alkali metal borohydride, such as sodium borohydride and the like, in a polar protic solvent, such as water, at a temperature of from about 50° C. to about 75° C. The pH for the reaction in this type solvent medium will normally range from about pH 6 to about pH 12. The starting keto-acid is dissolved in water containing a sufficient amount of an alkali metal hydroxide to maintain the pH within the aforesaid desired range. Upon completion of the reaction, the desired 4-(3,4-dichlorophenyl)-4-hydroxybutanoic acid intermediate is readily recovered from the reaction mixture in accordance with conventional procedure or used as such (i.e., in situ) in the next reaction step without any further treatment being necessary. When the reaction is conducted in an aqueous solvent medium as described above (pH 6), the hydroxy acid final product will normally be present in the form of an alkali metal salt.

The intermediate hydroxy acid formed in step (a) is then converted to the corresponding gamma-butyrolactone compound of structural formula (III) by first isolating the hydroxy acid from the reaction mixture as indicated above and thereafter heating said acid in an aromatic hydrocarbon solvent at a temperature that is in the range of from about 55° C. to about 150° C. until the conversion to the aforesaid lactone compound is substantially complete. Preferred aromatic hydrocarbon solvents for these purposes include those having from six to eight carbon atoms such as benzene, toluene, xylene and the like. Benzene is especially preferred in this connection as the reaction mixture can then be used directly in the next reaction step, i.e., the Friedel-Crafts type alkylation of step (c) without any isolation of the intermediate lactone compound being necessary.

Alternatively, the conversion of 4-(3,4-dichlorophenyl)-4-hydroxybutanoic acid which is formed in step (a) to the corresponding gamma-butyrolactone compound formed in step (b) is effected by heating the hydroxy acid in situ in an aqueous acid solvent medium at a temperature of from about 20° C. to about 100° C. until the conversion to the lactone compound of structural formula (III) is substantially complete. The aqueous acid solvent medium is preferably obtained by acidifying the warm aqueous alkaline solvent medium obtained in step (a); the latter medium also contains the intermediate hydroxy acid starting material of structural formula (IV) that had previously been formed in situ. The preferred acid for purposes of acidification in this connection is either hydrochloric acid or sulfuric acid, and the heating step (b) is preferably conducted at a temperature of from about 55° C. to about 80° C. until lactonization is substantially complete. Upon completion of this step, the final reaction mixture is slowly cooled to ambient temperatures and granulated in a conventional manner, while the desired 5-(3,4-dichlorophenyl)-dihydro-2(3H)furanone compound is thereafter preferably isolated from the mixture by using such means as suction filtration and the like, or else by means of extraction with a solvent, such as methylene chloride, which is also suitable for the next step.

The third and final stage of the multi-step process of the present invention involves reacting the gamma-lactone compound obtained in step (b) with benzene in an excess of said reagent as solvent or in a reaction-inert organic solvent in the presence of a Friedel-Crafts type catalyst at a temperature of from about 0° C. to about 100° C. until the alkylation of benzene by the gamma-lactone compound of formula (III) to form the desired final product of formula (I) is substantially complete. Preferred reaction-inert organic solvents for use in this particular alkylation step include carbon disulfide, nitrobenzene, various lower nitroalkanes like nitromethane and nitroethane, as well as halogenated benzene compounds such as o-dichlorobenzene and bromobenzene, in addition to various halogenated lower hydrocarbon solvents such as methylene chloride, ethylene dichloride, chloroform, trichloroethylene, s-tetrachloroethane and carbon tetrachloride, etc. The preferred Friedel-Crafts type catalyst for the reaction of step (c) is aluminum chloride. In a preferred embodiment of this particular step, the molar ratio of the gamma-butyrolactone compound of structural formula (III) employed as starting material in said step to the benzene reagent and the aluminum chloride catalyst is in the range of from about 1.0:1.0 to about 1.0:20.0 and from about 1.0:0.5 to about 1.0:10.0, respectively, with the preferred range that is directed to the optimum ratio being between about 1.0:2.0 and about 1.0:15.0 (gamma-butyrolactone/benzene) and between about 1.0:1.0 and about 1.0:2.0 (gamma-butyrolactone/aluminum chloride), respectively. Thus, for example, a most preferred optimum ratio has been found to about 1.0:2.5 in the case of gamma-butyrolactone/benzene and about 1.0:1.0 when dealing with the gamma-butyrolactone/aluminum chloride component. It is to be understood, of course, that the amount of benzene employed will be dependent upon whether it is also used as a solvent for the reaction or merely as a reagent in conjunction with another inert organic solvent of the type previously discussed (e.g., methylene chloride). The most preferred solvents for these purposes are therefore either benzene or a halogenated lower hydrocarbon solvent like methylene chloride, with the Friedel-Crafts alkylation reaction of step (c) being preferably conducted at a temperature of from about 10° C. to about 30° C. Upon completion of this step, the desired 4-(3,4-dichlorophenyl)-4-phenylbutanoic acid is readily recovered from the reaction mixture in a conventional manner common to Friedel-Crafts type reactions, viz., by first pouring the mixture onto stirred ice containing a mineral acid such as concentrated hydrochloric acid, followed by further stirring to effect a separation of the phases and subsequent isolation of the product from the organic phase, with the latter step being preferably accomplished by evaporation of the solvent therefrom and crystallization of the resulting residue, etc. In this way, the novel three-step process of this invention to prepare the valuable 4-(3,4-dichlorophenyl)-4-phenyl-butanoic acid from 4-(3,4-dichlorophenyl)-4-ketobutanoic acid is now complete.

In accordance with the more preferred alternate route of the process of this invention, the intermediate hydroxy acid formed in step (a), viz., 4-(3,4-dichlorophenyl)-4-hydroxybutanoic acid, or the gamma-butyrolactone compound formed in step (b), viz., 5-(3,4-dichlorophenyl)-dihydro-2(3H)-furanone, are each subjected to reaction with benzene in an excess of said reagent as solvent or in a reaction-inert organic solvent in the presence of a protic or Lewis acid catalyst at a temperature of from about −20° C. to about 180° C. until the alkylation of benzene by either the aforesaid hydroxy acid or the corresponding gamma-butyrolactone compound, followed by ring closure to form the desired ring ketone final product, viz., 4-(3,4-dichlorophenyl)-3,4-dihydro-1(2H)-naphthalenone, is substantially complete. Preferred reaction-inert organic solvents for use in this connection as cosolvents include the same solvents employed in step (c) of the three-step process, with the most preferred members being methylene chloride and o-dichlorobenzene. Preferred protic or Lewis acid catalysts for this particular reaction include (but are not limited to) sulfuric acid, trifluoromethanesulfonic acid, hydrofluoric acid, methanesulfonic acid, polyphosphoric acid, phosphorus pentoxide, aluminum chloride, phosphorus pentachloride, titanium tetrachloride and various acidic ion-exchange resins, with the most preferred members being the first four-named protic acids. In a preferred embodiment of this particular reaction, the molar ratio of hydroxy acid or gamma-butyrolactone starting material to the benzene reagent and the acid catalyst is in the range of from about 1.0:1.0 to about 1.0:20.0 and from about 1.0:0.1 to about 1.0:90.0, respectively, with the most preferred gamma-butyrolactone/benzene/acid catalyst ratios ranging from about 1.0:5.0:0.1 to about 1.0:10.0:90.0, respectively. In practice, the reaction is preferably conducted at a temperature ranging from about 15° C. up to about 145° C., with the most preferred temperature range being between about 15°-100° C. In the case where the acid catalyst employed is a protic acid such as sulfuric acid, trifluoromethanesulfonic acid or methanesulfonic acid, the preferred temperature range is generally between about 15°-100° C. as aforesaid and most preferably, between about 20°-100° C. In the case where the protic acid employed is hydrofluoric acid, the preferred temperature range is generally between about 15°-100° C. as aforesaid and most preferably, between about 15°-30° C. for the present purposes at hand. Upon completion of this step, the desired 4-(3,4-dichlorophenyl)-3,4-dihydro-1(2H)-naphthalenone is readily recovered from the reaction mixture in a conventional manner common for these type reactions, as previously set forth in greater detail in step (c) of the three-step process. In this way, the novel one-step alternate process of this invention for preparing 4-(3,4-dichlorophenyl)-3,4-dihydro-1(2H)-naphthalenone from either 5-(3,4-dichlorophenyl)-dihydro-2(3H)furanone or 4-(3,4-dichlorophenyl)-4-hydroxybutanoic acid is now complete.

The 4-(3,4-dichlorophenyl)-4-ketobutanoic acid ultimate starting material required for conducting the process of this invention is a known compound which can easily be synthesized by those skilled in the art starting from common chemical reagents and using conventional methods of organic synthesis. For instance, this particular compound is readily prepared by employing the method of E. A. Steck et al., as described in the *Journal of the American Chemical Society*, Vol. 75, p. 1117 (1953).

As previously indicated, the 4-(3,4-dichlorophenyl)-4-phenylbutanoic acid final product afforded by the principal process of this invention is a valuable intermediate that ultimately leads to the antidepressant agent known as sertraline or cis-(1S)(4S)-N-methyl-4-(3,4-dichlorophenyl)-1,2,3,4-tetrahydro-1-naphthaleneamine as disclosed in the previously discussed prior art. More specifically, 4-(3,4-dichlorophenyl)-4-phenylbutanoic acid is first converted to 4-(3,4-dichlorophenyl)-3,4-dihydro-1(2H)naphthalenone and then finally to racemic cis-N-methyl-4-(3,4-dichlorophenyl)-1,2,3,4-tetrahydro-1-naphthaleneamine prior to ultimately being converted to the desired cis-(1S)(4S)-N-methyl-4-(3,4-dichlorophenyl)-1,2,3,4-tetrahydro-1-naphthaleneamine by the multi-step method of the prior art process as earlier described by W. M. Welch, Jr. et al. in U.S. Pat. No. 4,536,518 and the *Journal of Medicinal Chemistry*, Vol. 27, No. 11, p. 1508 (1984). Moreover, the alternate route additionally provides a unique one-step method for converting either 4-(3,4-dichlorophenyl)-4-hydroxybutanoic acid or 5-(3,4-dichlorophenyl)-dihydro-2(3H)-furanone directly to 4-(3,4-dichlorophenyl)-3,4-dihydro-1(2H)-naphthalenone, which is then converted to sertraline as indicated above.

Hence, the novel process of the present invention now provides the required and valuable 4-(3,4-dichlorophenyl)-4-phenylbutanoic acid discussed above in pure form and in high yield by a unique three-step method, which represents a major improvement in view of the ease of synthesis and greatly reduced nature of the costs involved. Additionally, the alternate route represents a further saving in time and money in providing the direct obtention of 4-(3,4-dichlorophenyl)-3,4-dihydro-1(2H)-naphthalenone from either of the two novel intermediates of the present invention.

EXAMPLE 1

A 193 g. (0.781 mole) sample of 4-(3,4-dichlorophenyl)-4-ketobutanoic acid [E.A. Steck et al., *Journal of the American Chemical Society*, Vol. 75, p. 1117 (1953)] was slurried with 772 ml. of water in a reaction flask and heated to 70°–80° C., while 70 ml. of 15N aqueous sodium hydroxide (1.05 mole) were slowly added thereto over a period of one-half hour with the system being maintained within the pH range of 10.7–11.9. The pH value of the resulting dark brown solution was pH 11.7 (at 75° C.), at which point a solution consisting of 10.35 g. (0.272 mole) of sodium borohydride dissolved in 52.2 ml. of water containing 0.53 ml. of 15N aqueous sodium hydroxide (0.008 mole) was added thereto during the course of a one-half hour period. Upon completion of this step, the resulting reaction mixture was further stirred at this same temperature for a period of 45 minutes. Thin layer chromatography (T.L.C.) analysis of a sample taken at this point showed the complete absence of the keto-acid starting material. This solution now contained 4-(3,4-dichlorophenyl)-4-hydroxybutanoic acid in the form of the sodium salt.

A 50 ml. aliquot of the above alkaline solution (5% by volume) was then removed from the reaction flask and ice-cooled to 0°–10° C., while the pH was adjusted to pH 1.0 by the addition of 5N hydrochloric acid (with the temperature always being maintained below 10° C. throughout the course of this addition step). Upon completion of this step, the resulting solution was extracted with methylene chloride and the organic extracts were thereafter combined, washed with water and dried over anydrous sodium sulfate. After removal of the drying agent by means of filtration and the solvent by means of evaporation under reduced pressure, there were obtained 10 g. of 4-(3,4-dichlorophenyl)-4-hydroxybutanoic acid in the form of a brown-orange residual oil. The latter material was subsequently dissolved in 40 ml. of diethyl ether and to this solution there was added, in one portion, a solution consisting of 9.05 g. (0.05 mole) of dicyclohexylamine dissolved in 30 ml. of diethyl ether. The resulting crystalline slurry was then stirred and cooled to 10° C. for a period of one hour. In this way, there was readily obtained the corresponding crystalline dicyclohexylamine salt, which was thereafter recovered by means of suction filtration, washed with diethyl ether and dried in vacuo to constant weight to ultimately afford 9.6 g. of pure 4-(3,4-dichlorophenyl)-4-hydroxybutanoic acid (as the dicyclohexylamine salt), m.p. 152°–154° C. Recrystallization of the latter material (9.4 g.) from ethyl acetate (300 ml.) did not raise the melting point.

EXAMPLE 2

A mixture consisting of 370.62 g. (1.5 moles) of 4-(3,4-dichlorophenyl)-4-ketobutanoic acid [E. A. Steck et al., *Journal of the American Chemical Society*, Vol. 75, p. 1117 (1953)] and 1.505 liters of demineralized water was stirred and heated at 70°–80° C., while 130 ml. of 15N aqueous sodium hydroxide and 47.5 ml. of 1.5N aqueous sodium hydroxide were gradually added thereto in aliquot portions. The total time required for obtaining complete solution was approximately one hour, with the pH value of the resulting dark brown solution being pH 10.73 (at 78° C.). This solution was then transferred to a 5-liter flange flask and the temperature was maintained at ca. 65° C. (±3° C.), while a solution consisting of 19.86 g. (0.525 mole) of sodium borohydride dissolved in 100.3 ml. of demineralized water containing 1.03 ml. of 15N aqueous sodium hydroxide was added dropwise thereto during the course of a 44-minute period. Upon completion of this step, the resulting reaction mixture was further stirred at this same temperature for a period of approximately two hours. Thin layer chromatography (T.L.C.) analysis of a sample taken six minutes after completion of the addition step showed the complete absence of the keto-acid starting material. This solution now contained 4-(3,4-dichlorophenyl)-4-hydroxybutanoic acid in the form of the sodium salt. It was used as such (viz., in situ) in the next step of the process without any isolation of the product being necessary.

EXAMPLE 3

The warm aqueous alkaline solution containing 4-(3,4-dichlorophenyl)-4-hydroxybutanoic acid, as described in Example 2, was stirred and heated at 57°-62° C., while 5.8N hydrochloric acid (436 ml.) was slowly added dropwise thereto during the course of a 65-minute period with particular care being taken during the first one-half hour of the addition step due to the formation of a foam. Upon completion of this step, the resulting reaction mixture of oil and acidified water was vigorously stirred and heated at 65°-70° C. for a period of four hours prior to being allowed to cool to room temperature (ca.20° C.). Thin layer chromatography (T.L.C.) analysis of samples taken from the mixture at 1, 2, 2.5 and 3.5 hours after start of the final heating step showed that conversion of the hydroxy acid to the lactone was complete after 3.5 hours. The final mixture was allowed to gradually cool and granulate overnight for a period of approximately 16 hours, and the white-colored solid precipitate thus obtained was subsequently recovered by means of suction filtration and thereafter washed with two-80 ml. portions of demineralized water. After first air-drying on the filter funnel and then drying in vacuo at 46° C. in a vacuum oven overnight (ca. 16 hours), there were finally obtained 320 g. (92%) of pure 5-(3,4-dichlorophenyl)-dihydro-2(3H)-furanone, m.p. 64°-65° C.

EXAMPLE 4

To a well-stirred slurry consisting of 19.5 g. (0.25 mole) of benzene and 13.5 g. (0.10 mole) of aluminum chloride in 22.5 ml. of methylene chloride, there was added in a dropwise manner a solution consisting of 23.1 g. (0.10 mole) of 5-(3,4-dichlorophenyl)-dihydro-2(3H)-furanone (the product of Example 3) dissolved in 22.5 ml. of methylene chloride. The addition step was carried out during the course of a 15-minute period, during which time the temperature of the reaction mixture rose from 23° C. to 35° C. Upon completion of this step, the reaction mixture was stirred at room temperature (ca. 20° C.) for a period of two hours, during which time a dark brown solution resulted. Thin layer chromatography (T.L.C.) analysis of a sample of the mixture taken at the 1.5-hour mark revealed no starting material to be present at this point. The stirred mixture was next poured onto 100 g. of ice containing 20 ml. of concentrated hydrochloric acid, and the resulting aqueous acidic mixture was stirred for a period of 15 minutes. The organic phase of the resulting two-phase system was then separated and washed well with water, followed by atmospheric distillation to remove the methylene chloride. The residual liquid was then treated with hexane in a dropwise manner and allowed to cool to room temperature, which resulted in the precipitation of a light brown solid. The latter material was granulated at room temperature for a period of one hour, and finally recovered from the mixture by means of suction filtration and washed with a small portion of fresh hexane. After drying in vacuo to constant weight, there were ultimately obtained 28.0 g. (91%) of 4-(3,4-dichlorophenyl)-4-phenylbutanoic acid, m.p. 121°-122° C. [literature m.p. 118°-120° C., according to W. M. Welch, Jr. et al. in either U.S. Pat. No. 4,536,518 or *Journal of Medicinal Chemistry,* Vol. 27, No. 11, p.1508 (1984)]. A nuclear magnetic resonance spectrum of the material was found to be identical with that of an authentic sample prepared by the procedure described by W. M. Welch, Jr. et al. in the aforesaid prior art.

EXAMPLE 5

To a well-stirred slurry consisting of 126.4 g. (1.49 moles) of benzene and 86.4 g. (0.640 mole) of aluminum chloride contained in a 2-liter four-necked, round-bottomed reaction flask under a nitrogen atmosphere at 18° C., there was slowly added in a dropwise manner a solution consisting of 149.6 g (0.648 mole) of 5-(3,4-dichlorophenyl)-dihydro-2(3H)-furanone (the product of Example 3) dissolved in 800 ml. of benzene. The addition step was carried out during the course 50-minute period, during which time the temperature of the reaction mixture was maintained in the range of ca. 15°-20° C. with the aid of an ice bath. Upon completion of the step, the reaction mixture was stirred at room temperature (ca. 20° C.) for a period of two hours, during which time a brown solution resulted. The stirred mixture was next poured into 648 ml. of ice/water containing 129.6 ml. of concentrated hydrochloric acid at 1° C., and the resulting aqueous acidic mixture was stirred for a period of one-half hour. The organic phase of the resulting two-phase system was then separated from the aqueous phase, and the latter was saved and twice extracted with 100 ml. of benzene. The combined benzene layers were then filtered and thereafter subjected to vacuum distillation to remove the benzene. The off-white, golden tan solid residue which remained was then granulated with 500 ml. of hexanes for a period of 45 minutes, filtered and subsequently washed with three-100 ml. portions of fresh hexanes. The solid product and the hexane washes were then transfered to a 2000 ml. three-necked, round-bottomed flask and granulated for a period of approximately 16 hours. After filtering and washing the recovered product with another three-100 ml. portions of fresh hexanes, followed by vacuum drying at ca. 50° C., there were finally obtained 154.7 g. (77%) of pure 4-(3,4-dichlorophenyl)- 4-phenylbutanoic acid in the form of an off-white solid powder. This product was identical in every respect with the product of Example 4.

EXAMPLE 6

To a well-stirred slurry consisting of 126.22 g. 1.49 moles) of benzene (146.3 ml.) and 86.4 g. of (0.640 mole) of aluminum chloride in 186 ml. of o-dichlorobenzene contained in a 2-liter four-necked, round-bottom reaction flask under a nitrogen atmosphere at 7° C., there was slowly added in a dropwise manner a solution consisting of 149.6 g. (0.648 mole) of 5-(3,4-dichlorophenyl)-dihydro-2(3H)-furanone (the product of Example 3) dissolved in 600 ml. of o-dichlorobenzene. The addition step was carried out during the course of a 2.5-hour period, during which time the temperature of the reaction mixture was maintained in the range of ca. 7°-9° C. with the aid of an ice bath. Upon completion of this step, the reaction mixture was stirred at room temperature (ca. 20° C.) for a period of 35 minutes and then quenched into a mixture of 650 ml. of water and 130 ml. of concentrated hydrochloric acid at −4° C., with the temperature of the resulting aqueous acidic mixture always being maintained below 28° C. throughout the course of the quenching step. The latter mixture (now a white slurry) was stirred for a period of ten minutes and then allowed to separate into two layers. The saved organic layer was washed twice with an equal volume of warm water, and a 550 ml. aliquot of this washed layer was then transferred into a 3-liter four-necked, round-bottomed flask and charged with 500 ml. of water and 60 ml. of 50% aqueous sodium hydroxide solution, followed by stirring for a period of ten minutes. The resulting organic layer was then separated from the aqueous caustic layer and re-extracted once again with 500 ml. of 50% aqueous sodium hydroxide. The combined aqueous caustic layers were next extracted with 300 ml. of methylene chloride, and the latter organic layer was thereafter separated, saved and then subjected to vacuum distillation to remove most of the methylene chloride. After seeding the residual thick liquid material with a pinch of authentic 4-(3,4-dichlorophenyl)-4-phenylbutanoic acid (prepared as in Example 4), followed by stirring for a period of approximately one-half hour, there resulted a very thick crystalline slurry which was thereafter charged with 400 ml. of heptane. The resulting mixture was then stirred for a period of approximately 16 hours (i.e., overnight), filtered and the crystalline product subsequently recovered by means of suction filtration and washed with a fresh portion of heptane to afford a white solid material. After repulping the latter product with 500 ml. of hexane, and then filtering and drying same in a vacuum oven to constant weight, there were ultimately obtained 82.0 g. (41%) of pure 4-(3,4-dichlorophenyl)-4-phenylbutanoic acid identical in every respect with the product of Example 4.

EXAMPLE 7

In a 25 ml. round-bottomed reaction flask equipped with reflux condenser, there were placed 8.0 g. (0.083 mole) of methanesulfonic acid. The latter substance was then heated to 95° C., at which point a solution consisting of 1.0 g. (0.004 mole) of 5-(3,4-dichlorophenyl)-dihydro-2(3H)-furanone (the product of Example 3) dissolved in 2 ml. (0.022 mole) of benzene was added thereto in a dropwise manner during the course of a 20-minute period. Upon completion of this step, the reaction mixture was stirred at 95° C. for a period of seven hours and then cooled and inversed quenched onto 60 g. of ice. When the quenched reaction mixture had warmed to ambient temperature (ca. 20° C.), it was extracted with three-30 ml. portions of diethyl ether. The separated ether layers were then combined and backwashed with saturated aqueous sodium bicarbonate solution, followed by drying over anhydrous magnesium sulfate. After removal of the drying agent by means of filtration and the solvent by means of evaporation under reduced pressure, there was finally obtained a residual oil which proved to be crude 4-(3,4-dichlorophenyl)-3,4-dihydro-1(2H)-naphthalenone. The latter material was subsequently chromatographed on 20 g. of 70-230 mesh silica gel, using 25% ethyl acetate/hexane as the eluant. In this manner, there was ultimately obtained 724 mg. (62%) of pure 4-(3,4-dichlorophenyl)-3,4-dihydro-1(2H)-naphthalenone identical in every respect with the product of Example 1(E) of U.S. Pat. No. 4,536,518.

EXAMPLE 8

In a 20 ml. round-bottomed reaction flask equipped with a reflux condenser, there was placed 1.0 g. (0.004 mole) of 5-(3,4-dichlorophenyl)-dihydro-2(3H)-furanone (the product of Example 3), 4 ml. (0.045 mole) of benzene and 5 ml. of 96% sulfuric acid (0.094 mole), all being added at ambient temperature (ca. 20° C.). The resulting reaction mixture was then heated at 95° C. for a period of one hour and thereafter at 140° C. for 1.5 hours. Upon completion of this step, the reaction mixture was cooled to ambient temperature and then inversed quenched onto 40 g. of ice. After stirring the resulting aqueous mixture at ambient temperature for a period of 18 hours, the pale green solid product was recovered by means of suction filtration and air dried to constant weight. In this manner, there was ultimately obtained 740 mg. (63%) of good quality 4-(3,4-dichlorophenyl)-3,4-dihydro-1(2H)-naphthalenone containing only a trace of 4-(3,4-dichlorophenyl)-4-phenylbutanoic acid, as evidenced via thin layer chromatography (T.L.C.) analysis and high field proton and carbon nuclear magnetic resonance data.

EXAMPLE 9

In a 250 ml. round-bottomed reaction flask equipped with a reflux condenser, there were placed 10 g. (0.04 mole) of 5-(3,4-dichlorophenyl)-dihydro-2(3H)-furanone (the product of Example 3), 20 ml. (0.22 mole) of benzene and 80 g. (0.830 mole) of methanesulfonic acid at ambient temperature (ca. 20° C.). The reaction mixture was then heated at 100° C. for a period of 20 hours. Upon completion of this step, the reaction mixture was cooled to ambient temperature and then inversed quenched onto 200 g. of ice. At this point, 50 ml. of methylene chloride were added and the pH of the aqueous phase was adjusted to pH 11.3 with 167 ml. of 20% aqueous sodium hydroxide. Another 50 ml. portion of methylene chloride was then added to the basified aqueous mixture, and the aqueous phase was extracted. The separated aqueous layer was extracted again with 50 ml. of methylene chloride, and the combined organic extracts were subsequently dried over anhydrous magnesium sulfate, filtered and thereafter subjected to atmospheric distillation to remove the solvent. During the distillation step, the methylene chloride was also displaced with a total of 50 ml. of hexanes and 75 ml. of isopropyl ether. When the total volume of the residual distilland had been reduced to ca. 90 ml., the reaction solution was allowed to cool to ambient temperature with constant agitation. After stirring at this point (i.e.-,at ca 20° C.) for a period of 18 hours, the light yellow solid product was recovered by means of suction filtration and air dried to constant weight. In this way, there were ultimately obtained 7.24 g. (62%) of good quality 4-(3,4-dichlorophenyl)-3,4-dihydro-1(2H)-napthalenone.

EXAMPLE 10

The procedure described in Example 7 was repeated except that polyphosphoric acid was the acid catalyst employed in place of methanesulfonic acid, using the same molar proportions as before. In this particular case, the corresponding final product obtained was also pure 4-(3,4-dichlorophenyl)-3,4-dihydro-1(2H)-naphthalenone. Similar results were also obtained when phosphorus pentoxide, aluminum chloride and titanium tetrachloride were each individually employed in place of methanesulfonic acid, again using the same molar proportions as before.

EXAMPLE 11

A 25 ml. aliquot of the aqueous alkaline solution containing 4-(3,4-dichlorophenyl)-4-hydroxybutanoic acid (5.0 g., 0.018 mole), prepared as described in Example 2, was treated with 25 ml. of methylene chloride and the pH of the aqueous phase was adjusted to pH 1.0 with 96% sulfuric acid (1.5 ml.). The two layers were then separated, and the resulting organic extract was transferred into a 100 ml. round-bottomed reaction flask equipped with distillation apparatus. At this point, 25 ml. (0.28 mole) of benzene were added and the methylene chloride solvent was removed by means of atmospheric distillation. Thereafter, an additional 25 ml. of 96% sulfuric acid (0.48 mole) and 5 ml. (0.056 mole) of benzene were added to the residual distilland, and the reaction flask containing same was thereafter fitted with a reflux condenser after the distillation apparatus had first been removed. The reaction mixture contained in the flask was then heated at 95° C. for a period of one hour and thereafter at 135° C. for three hours. Upon completion of this step, the resulting mixture was cooled to ambient temperature (ca. 20° C.) and then inversed quenched onto 200 g. of ice. The resulting aqueous phase was next twice extracted with methylene chloride (50 ml./10 ml.), and the combined organic extracts were subsequently dried over anhydrous magnesium sulfate and filtered. After removal of the drying agent by means of filtration and the solvent by means of evaporation under reduced pressure, there were finally obtained 2.89 g. of residual material in the form of a yellow foam. Thin layer chromatography analysis (T.L.C) and high field proton nuclear magnetic resonance data then showed the major component of the foam to be 4-(3,4-dichlorophenyl)-3,4-dihydro-1(2H)-naphthalenone.

EXAMPLE 12

In a 125 ml. polypropylene reaction vessel, there were placed 3.0 g. (0.012 mole) of 5-(3,4-dichlorophenyl)-dihydro-2(3H)-furanone (the product of Example 3) dissolved in 6 ml. (0.067 mole) of benzene. The reaction vessel was then attached to a polypropylene manifold, and 20 ml. (1.0 mole) of anhydrous hydrofluoric acid (hydrogen fluoride) was distilled into the vessel containing the aforesaid benzene solution at −78° C. The reaction mixture was then allowed to warm to ambient temperature (ca. 20° C.) and thereafter stirred at that point for a period of 18 hours. Upon completion of this step, the excess hydrofluoric acid and benzene were removed from the mixture by means of vacuum distillation and the recovered hydrofluoric acid was thereafter scrubbed with calcium oxide. The system was then purged with nitrogen, and the reaction vessel was subsequently removed from the hydrofluoric acid manifold. At this point, 30 ml. of methylene chloride and 5 ml. of water were added to the polypropylene reaction vessel and its contents which were then cooled to 0° C. Aqueous sodium hydroxide (1.0N) was thereafter added to the reaction system until the pH of the aqueous solution was adjusted to a value of pH 12.0 (this required 13 ml. of added base). The resulting organic layer was then separated from the two-phase system and the aqueous layer extracted again with 30 ml. of methylene chloride. The combined organic layers were next dried over anhydrous magnesium sulfate and filtered, and the resulting organic filtrate thereafter transferred to a 125 ml. round-bottomed flask prior to being concentrated via atmospheric distillation. After the volume had first been reduced to ca. 30 ml., hexane (40 ml.) was added and distillation was resumed until the distillate reached a temperature of 67° C. At this point, the heating mantel was removed and within a period of five minutes a white precipitate commenced forming. After stirring the resulting white suspension for a period of 16 hours, the fully-precipitated white solid product was recovered by means of filtration and subsequently dried in a vacuum oven to constant weight. In this way, there were ultimately obtained 3.43 g. (97%) of good quality 4-(3,4-dichlorophenyl)-3,4-dihydro-1(2H)-naphthalenone, m.p. 102°–103° C. The pure product was further characterized by means of thin layer chromatography (T.L.C.) analysis, and high field proton and carbon nuclear magnetic resonance data.

EXAMPLE 13

In a 25 ml. round-bottomed reaction flask equipped with a reflux condenser, there were placed 3.0 g. (0.012 mole) of 5-(3,4-dichlorophenyl)-dihydro-2(3H)furanone (the product of Example 3) dissolved in 6 ml. (0.067 mole) of benzene. To the stirred benzene solution, there were then added 5.34 ml. (0.060 mole) of trifluoromethanesulfonic acid at ambient temperature (ca. 20° C.), followed by further stirring at this point for a period of five minutes. The resulting reaction mixture was then heated at 75° C. for a period of 1.5 hours and finally allowed to cool to ambient temperature. Upon completion of this step, the final mixture was inversed quenched onto 20 g. of ice and thereafter treated with 30 ml. of methylene chloride. The quenched reaction mixture was next basified with 15 ml. of 4N aqueous sodium hydroxide solution so as to adjust the pH of the aqueous medium to pH 9.0. At this point, the two layers were separated and the aqueous layer was extracted again with 30 ml. of methylene chloride. The organic layers were then combined and subsequently dried over anhydrous magnesium sulfate, followed by filtration and transfer of the resulting filtrate into a 125 ml. round-bottomed distillation flask. The methylene chloride solvent was next removed by means of atmospheric distillation until the volume of the distilland in the flask had been reduced to ca. 40 ml., at which point 40 ml. of hexane were added and distillation was resumed until the distillate reach a temperature of 67° C. At this point, the heating mantel was removed and within a period of five minutes a white precipitate commenced forming. After stirring the resulting white suspension for a period of 16 hours, the fully-precipitated white solid product was recovered by means of filtration and subsequently dried in a vacuum oven to constant weight. In this way, there were ultimately obtained 3.22 g. (91%) of good quality 4-(3,4-dichlorophenyl)-3,4-dihydro-1(2H)naphthalenone, m.p. 103°–104° C. The pure product was further characterized by means of thin layer chromatography (T.L.C.) analysis, and high field proton and carbon nuclear magnetic resonance data.

We claim:

1. A process for preparing 4-(3,4-dichlorophenyl)-3,4-dihydro-1(2H)-naphthalenone, which comprises reacting 4-(3,4-dichlorophenyl)-4-hydroxybutanoic acid or 5-(3,4-dichlorophenyl)-dihydro-2(3H)-furanone with benzene in an excess of said reagent as solvent or in a reaction-inert organic solvent in the presence of a protic or Lewis acid catalyst at a temperature of from about −20° C. to about 180° C. until the alkylation of benzene by either the aforesaid hydroxy acid or the corresponding gamma-butyrolactone compound, followed by ring closure to form the desired ring ketone final product is substantially complete.

2. A process as claimed in claim 1 wherein the acid catalyst employed is a protic acid.

3. A process as claimed in claim 2 wherein the protic acid is sulfuric acid.

4. A process as claimed in claim 2 wherein the protic acid is trifluoromethanesulfonic acid.

5. A process as claimed in claim 2 wherein the protic acid is hydrofluoric acid.

6. A process as claimed in claim 2 wherein the protic acid is methanesulfonic acid.

7. A process as claimed in claim 1 wherein the molar ratio of hydroxy acid or gamma-butyrolactone starting material to the benzene reagent and the acid catalyst is in the range of from about 1.0:1.0 to about 1.0:20.0 and from about 1.0:0.1 to about 1.0:90.0, respectively.

8. A process as claimed in claim 7 wherein the gamma-butyrolactone/benzene/acid catalyst molar ratio is about 1.0:5.0:20.0.

9. A process as claimed in claim 7 wherein the gamma-butyrolactone/benzene/acid catalyst molar ratio is about 1.0:10.0:20.0.

10. A process as claimed in claim 7 wherein the hydroxy acid/benzene/acid catalyst molar ratio is about 1.0,15.0:30.0.

11. A process as claimed in claim 7 wherein the gamma-butyrolactone/benzene/acid catalyst molar ratio is about 1.0:5.5:90.

12. A process as claimed in claim 7 werein the gamma-butyrolactone/benzene/acid catalyst molar ratio is about 1.0:5.5:5.0.

13. A process as claimed in claim 1 wherein the reaction is conducted at a temperature of from about 15° C. to about 145° C.

14. A process as claimed in claim 2 wherein the reaction is conducted at a temperature of from about 15° C. to about 100° C.

15. A process as claimed in claim 14 wherein the protic acid is sulfuric acid, trifluoromethanesulfonic acid or methanesulfonic acid and the reaction is conducted at a temperature of at least about 20° C.

16. A process as claimed in claim 14 wherein the protic acid is hydrofluoric acid and the reaction is conducted at a temperature of below about 30° C.

17. A process as claimed in claim 1 wherein the reaction-inert organic solvent employed as cosolvent is methylene chloride.

18. A process as claimed in claim 1 wherein the reaction-inert organic solvent employed as cosolvent is o-dichlorobenzene.

19. A process as claimed in claim 1 wherein the reaction is conducted by using an excess of benzene as the solvent.

* * * * *